United States Patent
Abramovici et al.

(12) 
(10) Patent No.: US 6,528,539 B1
(45) Date of Patent: Mar. 4, 2003

(54) STABLE FORMULATION CONTAINING FUMAGILLIN

(75) Inventors: Bernard Abramovici, Juvignac (FR); Jean-Luc Dubois, Vacquieres (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/913,547

(22) PCT Filed: Feb. 21, 2000

(86) PCT No.: PCT/FR00/00424

§ 371 (c)(1),
(2), (4) Date: Oct. 15, 2001

(87) PCT Pub. No.: WO00/50084

PCT Pub. Date: Aug. 31, 2000

(30) Foreign Application Priority Data

Feb. 26, 1999 (FR) .............................................. 99 02401
Jul. 27, 1999 (FR) .............................................. 99 09702

(51) Int. Cl.⁷ ........................ A61K 31/335; A61K 9/48; A61K 9/52; A61K 9/20; A61K 9/22
(52) U.S. Cl. ........................ 514/475; 514/937; 514/938; 514/944; 514/943; 424/451; 424/457; 424/464; 424/468

(58) Field of Search ................................. 514/475, 962, 514/937, 938, 944; 424/451, 457, 464, 468

(56) References Cited

U.S. PATENT DOCUMENTS

| 4,918,103 | A |   | 4/1990  | Park et al. ................... 514/520 |
| 5,846,562 | A | * | 12/1998 | Yanai et al. ................. 424/451 |
| 5,900,431 | A |   | 5/1999  | Molina et al. ............... 514/475 |
| 6,267,985 | B1 | * | 7/2001  | Chen et al. ................. 424/451 |
| 6,316,497 | B1 | * | 11/2001 | Liu et al. .................... 514/475 |

FOREIGN PATENT DOCUMENTS

| EP | 0 602 586 | 6/1994 |
| EP | 0 799 616 | 10/1997 |
| WO | WO 96/30010 | 10/1996 |

* cited by examiner

*Primary Examiner*—Zohreh Fay
*Assistant Examiner*—Brian-Yong S. Kwon
(74) *Attorney, Agent, or Firm*—Michael D. Alexander; Paul E. Dupont

(57) ABSTRACT

The invention relates to a stable fumagillin formulation and to the method of use thereof in treating and/or combating intestinal infections.

20 Claims, No Drawings

STABLE FORMULATION CONTAINING FUMAGILLIN

CROSS REFERENCE TO RELATED APPLICATIONS

This application is a 35 U.S.C. 371 application of PCT International application No. PCT/FR00/00424, filed Feb. 21, 2000, which in turn claims priority from French application No. 99/02401, filed Feb. 26, 1999 and French application No. 99/09702, filed Jul. 27, 1999.

The present invention relates to a stable fumagillin formulation. In particular, the present invention relates to a stable fumagillin formulation for oral or rectal administration.

Fumagillin is an antibiotic which was first described in 1951 (The Merck Index, 12th edition, No. 4308). Originally, fumagillin was used to prevent or combat parasitic diseases in fish farms and apiaries. More recently, fumagillin has been found to be of interest in human therapy. In particular, reference may be made to patent application WO 96/30010 which points out the efficacy of fumagillin in treating intestinal infections caused by microsporidae and/or cryptosporidae especially in patients who have contracted the HIV virus.

Fumagillin, 2,4,6,8-decatetraenedioic acid mono[4-(1,2-epoxy-1,5-dimethyl-4-hexenyl)-5-methoxy-1-oxaspiro[2.5]oct-6-yl] ester of formula:

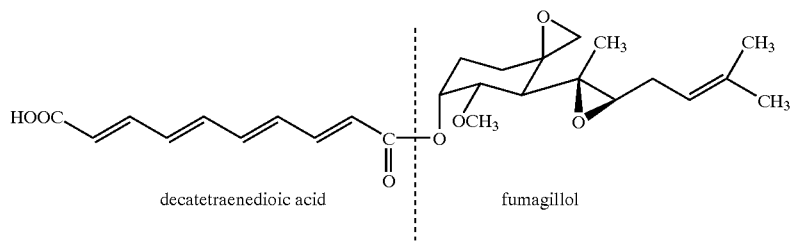

decatetraenedioic acid     fumagillol is highly unstable at ambient temperature and must be stored at −80° C. Fumagillin contains many functions that are unstable: unstable at ambient temperature, unstable to light, readily oxidizable or hydrolyzable. Reference may be made to various studies carried out on fumagillin, in particular in: J. Agric. Food Chem. 1991, 39, 2206–2213; J. Pharm. Sci. 1976, 65(1), 1–22; J. Amer. Chem. Soc. 1955, 77, 5610–5617 and J. Amer. Pharm. Ass., Sci. Ed. 1954, 43, 536–543. The various degradations which fumagillin may undergo are thus mainly due to the presence of the epoxy functions, the ester function and the conjugated double bonds. In order for fumagillin to be able to be used as medicinal products, a pharmaceutical formulation which is stable at ambient temperature and easy to store must be prepared.

Certain stable compositions of fumagillol derivatives have already been described.

For example, patent EP 602 586 describes stable pharmaceutical compositions containing a fumagillol derivative and a fatty acid ester of glycerol or of polyglycerol. Patent application EP 799 616 describes pharmaceutical compositions for oral administration comprising a fumagillol derivative and an oleaginous base, said compositions being stable with respect to gastric acid. Neither of these documents specifically describes a fumagillin formulation.

According to the present invention, it is has now been found that in the case of fumagillin, by using a hydrophobic agent: propylene glycol dicaprate/dicaprylate ester, a stable formulation is obtained. A fumagillin formulation which is stable at ambient temperature is thus obtained, without adding a stabilizer or an antioxidant.

The propylene glycol dicaprate/dicaprylate ester, also known as propylene glycol dicaprylocaprate, is sold under the brand name Labrafac® PG.

Thus, the present invention relates to a stable, orally administrable formulation containing fumagillin and propylene glycol dicaprate/dicaprylate.

In particular, the formulation according to the present invention is in the form of a gel capsule or a soft capsule containing fumagillin and propylene glycol dicaprate/dicaprylate. The capsule or gel capsule is preferably non-translucent, for example colored or opaque white. In order to ensure the leaktightness of these formulations, said gel capsules or capsules may be hoop-cased or sealed.

The LEMS (Liquid Encapsulation by Micro Spray) process is carried out continuously directly on leaving the machines for filling the gel capsules (LEMS capsugel). It consists in sealing Licaps gel capsules by a process of pulverization-spraying with aqueous-alcoholic liquid and drying to allow self-bonding of the gelatin between the body and the cap of the gel capsule, thus ensuring the desired leaktightness.

In the conventional hoop casing process, the gel capsules obtained from the filling machines are positioned on a hoop casing machine comprising a gel capsule support belt (the capsules being laid flat in alveolae and in contact with a lower disc. Under the conveyor belt are positioned vertical discs which, by rotating in a gelatin solution, deposit a strip of gelatin between the body and the cap of the gel capsule; where necessary, the gel capsules may be treated twice, that is to say a double hoop casing since, during the first treatment, air microbubbles may be generated in the strip of gelatin deposited. This is a safety operation with regard to the leaktightness.

A formulation in the form of a gel capsule (or capsule) containing a gel capsule (or capsule, respectively) of smaller size containing fumagillin and propylene glycol dicaprate/dicaprylate may also be used.

According to another of its aspects, the present invention relates to drinkable liquid formulations containing a mixture of fumagillin and propylene glycol dicaprate/dicaprylate. These formulations may be in the form of syrup preferably stored in a multidose flask or in the form of a liquid packaged as a single dose ampule. Preferably, the flasks or ampules used are nontranslucent, for example made of brown glass.

A subject of the present invention is also stable, rectally administrable formulations containing fumagillin and propylene glycol dicaprate/dicaprylate. These compositions are preferably packaged in a single dose container with a cannula. The formulations according to the invention advantageously comprise 0.2% to 15% (w/w) and preferably 5% to 12% (w/w) of fumagillin.

The formulations according to the invention may also contain other pharmaceutical excipients. A thixotropic or viscosity-modifying agent may be used in particular, such as, for example, colloidal silica: Aerosil® R972 or Aerosil® R974, or alternatively ethylcellulose, Aerosil® R972 being preferred.

The formulations are prepared as follows: the fumagillin is added to the propylene glycol dicaprate/dicaprylate with gentle stirring in order to homogenize the mixture. The gel capsules are then filled with this mixture by means of a semiautomatic machine.

A subject of the present invention is also the use of these stable fumagillin formulations to prepare medicinal products for treating intestinal infections caused by microsporidae and/or cryptosporidae, and also for treating said infections.

More particularly, the invention relates to the use of these formulations in AIDS patients and for intestinal infections whose main causative agent is the parasite *Enterocytozoon bieneusi*.

The daily dose of active principle to be administered naturally varies according to the age and weight of the patient, and also according to the type and severity of the pathology to be treated.

In general, for an adult of normal constitution, the daily dose of active principle to be administered according to the invention is between 1 and 100 mg, preferably between 40 and 80 mg and in particular 60 mg.

The unit forms may contain from 1 to 100 mg of active principle, advantageously from 5 to 50 mg or preferably from 7 to 30 mg, in particular 20 mg. Such unit doses are generally administered 1 to 4 times a day, preferably 3 times a day. This type of treatment lasts from 1 to 4 weeks, preferably 2 weeks.

EXAMPLE 1

| Constituent | Unit formulation |
| --- | --- |
| Fumagillin | 20 mg |
| Labrafac ®PG | 215 mg | for a size 0 "opaque-white" Licaps gel capsule filled with 235 mg

Mixing

The Labrafac®PG is incorporated into a suitable container. The active principle is added gradually with very gentle stirring, and stirring is continued until a homogeneous solution is obtained.

Filling

The size 0 "opaque-white" gel capsules of Licaps type, with a theoretical weight of 235 mg, are filled with the above mixture with the aid of a "Hibar" semiautomatic machine.

EXAMPLE 2

| Constituent | Unit formulation |
| --- | --- |
| Fumagillin | 20 mg |
| Labrafac ®PG | 400 mg | for a size 0 op.C314 Swedish orange Licaps gel capsule filled with 420 mg

EXAMPLE 3

| Constituent | Unit formulation |
| --- | --- |
| Fumagillin | 20 mg |
| Labrafac ®PG | 215 mg | for a size 3 op.C314 Swedish orange Licaps gel capsule filled with 235 mg

EXAMPLE 4

| Constituent | Unit formulation |
| --- | --- |
| Fumagillin | 20 mg |
| Aerosil ® R972 | 11.75 mg |
| Labrafac ®PG | 223.25 mg | for a size 3 "opaque-white" Licaps gel capsule filled with 250 mg

EXAMPLE 5

| Constituent | Unit formulation |
| --- | --- |
| Fumagillin | 20 mg |
| Aerosil ® R972 | 25 mg |
| Labrafac ®PG | 475 mg | for a size 0 op.C314 Swedish orange Licaps gel capsule filled with 520 mg

EXAMPLE 6

| Constituent | Unit formulation |
| --- | --- |
| Fumagillin | 20 mg |
| Labrafac ®PG | qs 5 ml |

5 ml brown glass drinkable ampule

EXAMPLE 7

| Constituent | Unit formulation |
| --- | --- |
| Fumagillin | 200 mg |
| Labrafac ®PG | qs 10 ml |

10 ml brown glass multidose bottle

EXAMPLE 8

| Constituent | Unit formulation |
| --- | --- |
| Fumagillin | 20 mg |
| Aerosil ® R972 | 25 mg |
| Labrafac ®PG | 475 mg | for a finished opaque-white soft capsule containing 520 mg

EXAMPLE 9

| Constituent | Unit formulation |
|---|---|
| Fumagillin | 20 mg |
| Aerosil ® R972 | 50 mg |
| Labrafac ®PG | 950 mg | rectal gel in single-dose container with cannula

EXAMPLE 10

| Constituent | Unit formulation |
|---|---|
| Fumagillin | 20 mg |
| Aerosil ® R972 | 250 mg |
| Labrafac ®PG | 4750 mg |

Rectal gel in single dose container with cannula

EXAMPLE 11

| Constituent | Unit formulation |
|---|---|
| Fumagillin | 20 mg |
| Labrafac ®PG | 215 mg | for a size 1 "opaque-white" Licaps gel capsule filled with 235 mg

EXAMPLE 12

| Constituent | Unit formulation |
|---|---|
| Fumagillin | 20 mg |
| Aerosil ® R972 | 16 mg |
| Labrafac ®PG | 214 mg | for a size 1 "opaque-white" Licaps gel capsule filled with 250 mg.

EXAMPLE 13

| Constituent | Unit formulation |
|---|---|
| Fumagillin | 20 mg |
| Labrafac ®PG | 215 mg | for a size 1 "opaque-white" Licaps gel capsule filled with 235 mg, contained in a size 0 "opaque-white" Licaps gel capsule

EXAMPLE 14

Size 1 "opaque-white" Licaps gel capsule according to Example 11 or 12, hoop cased with the following hoop casing formulation: Hoop casing formulation for a gel capsule

| Constituent | Unit formulation |
|---|---|
| 200 blooms gelatin | 0.192 mg |
| Purified water* | 2.208 mg |

*removed during the process (drying)

EXAMPLE 15

"Opaque-white" Licaps gel capsule according to Example 11 or 12, sealed with the following hoop casing formulation: sealing formulation (LEMS machine): aqueous-alcoholic solution (50/50) (removed during the process).

An aqueous-alcoholic solution is sprayed onto the gel capsules and drying is carried out at a temperature of 44° C. The water lowers the Tg (glass transition) of the gelatin. The alcohol lowers the surface tension and allows capillary ascension between the body and the cap. The temperature increase allows the evaporation and the self-fusion of the gelatin.

What is claimed is:

1. A stable formulation consisting essentially of fumagillin and propylene glycol dicaprate/dicaprylate.
2. A stable formulation consisting essentially of fumagillin, propylene glycol dicaprate/dicaprylate and a thixotropic agent.
3. A stable formulation according to claim 2 wherein the thixotropic agent is colloidal silica.
4. A stable formulation according to claim 1 which is orally administrable.
5. A stable formulation according to claim 4 in the form of a gel capsule or a capsule.
6. A stable formulation according to claim 5 in the form of a sealed capsule or gel capsule.
7. A stable formulation according to claim 5 in the form of a hoop cased capsule or gel capsule.
8. A stable formulation according to claim 5 wherein the gel capsule or the capsule is non-translucent.
9. A stable formulation according to claim 4 which is drinkable.
10. A stable formulation according to claim 9 in the form of a syrup stored in a non-translucent multidose bottle or single dose ampule.
11. A stable formulation according to claim 1 which is rectally administrable.
12. A stable formulation according to claim 1 wherein it contains 0.2% to 15% (w/w) of fumagillin.
13. A stable formulation according to claim 1 wherein it contains 8% to 10% (w/w) of fumagillin.
14. A stable formulation according to claim 13 wherein it contains 20 mg of fumagillin and 215 mg of propylene glycol dicaprate/dicaprylate in a gel capsule.
15. A stable formulation according to claim 2 which is orally administrable.
16. A stable formulation according to claim 3 which is orally administrable.
17. A stable formulation according to claim 15 in the form of a gel capsule or a capsule.
18. A stable formulation according to claim 16 in the form of a gel capsule or capsule.
19. A stable formulation according to claim 17 wherein the gel capsule or the capsule is non-translucent.
20. A stable formulation according to claim 18 wherein the gel capsule or the capsule is non-translucent.

* * * * *